United States Patent
Viswanathan

(10) Patent No.: US 6,587,706 B1
(45) Date of Patent: Jul. 1, 2003

(54) MICROCOIL DEVICE WITH A FORWARD FIELD-OF-VIEW FOR LARGE GAIN MAGNETIC RESONANCE IMAGING

(75) Inventor: Raju R. Viswanathan, Towson, MD (US)

(73) Assignee: Image-Guided Drug Delivery Systems, Inc., Minneapolis, MN (US)

(*) Notice: Subject to any disclaimer, the term of this patent is extended or adjusted under 35 U.S.C. 154(b) by 0 days.

(21) Appl. No.: 09/532,037

(22) Filed: Mar. 21, 2000

Related U.S. Application Data

(63) Continuation-in-part of application No. 09/448,720, filed on Nov. 24, 1999, which is a continuation-in-part of application No. 09/131,031, filed on Aug. 7, 1998, and a continuation-in-part of application No. 08/916,596, filed on Aug. 22, 1997, now Pat. No. 5,964,705.

(51) Int. Cl.[7] .............................................. A61B 5/055
(52) U.S. Cl. ........................ 600/410; 600/411; 600/421; 600/422; 600/423; 324/300; 324/301; 324/313; 324/318; 324/322
(58) Field of Search ................................ 600/407, 409, 600/410, 411, 419, 423, 425, 427, 9, 10, 11–13; 604/19, 21; 607/101, 104; 324/300, 301, 313, 318, 322, 219

(56) References Cited

U.S. PATENT DOCUMENTS

| | | | |
|---|---|---|---|
| 4,572,198 A | 2/1986 | Codrington | 128/653 |
| 5,271,400 A | 12/1993 | Dumoulin et al. | 128/653.2 |
| 5,357,958 A | 10/1994 | Kaufman | 128/653.2 |
| 5,964,705 A | 10/1999 | Truwit et al. | 600/423 |
| 6,026,316 A | 2/2000 | Kucharczyk et al. | 600/420 |
| 6,061,587 A | 5/2000 | Kucharcyzk et al. | 600/411 |
| 6,272,370 B1 * | 8/2001 | Gillies et al. | 324/309 |

FOREIGN PATENT DOCUMENTS

| | | | |
|---|---|---|---|
| EP | 0928972 A2 | 7/1999 | G01R/33/28 |
| WO | WO 99/10035 | 3/1999 | A61M/25/00 |

OTHER PUBLICATIONS

Hurst, G.C., et al.: "Intravascular (Catheter) NMR Receiver Probe: Preliminary Design Analysis and Application to Canine Iliofemoral Imaging," *Magnetic Resonance In Medicine* 24 (1992) Apr., No. 2, pp. 343–357.

Atalar, E., et al., "High Resolution Intravascular MRI and MRS by Using a Catheter Receiver Coil", *Magnetic Resonance In Medicine*, 36 (4), pp. 596–605, (Oct. 1996).

Martin, A.J., et al., "MR Imaging of Blood Vessels with an Intravascular Coil", *Journal of Magnetic Resonance Imaging*, 2 (4), pp. 421–429, (1992).

* cited by examiner

Primary Examiner—Marvin M. Lateef
Assistant Examiner—Jeoyuh Lin
(74) Attorney, Agent, or Firm—Mark A. Litman & Assoc. P.A.

(57) ABSTRACT

Microcoils can be used in medical devices to enhance RF response signals and to create fields to enhance imaging capability in MRI imaging systems. An improved microcoil design includes a device to be inserted into a patient comprising a solid body having at least one pair of radially opposed microcoils physically associated with the solid body, each microcoil having an outside microcoil diameter of 6 mm or less, individual windings of each microcoil together defining a geometric plane for each microcoil, and the plane of each microcoil being parallel to the plane of another microcoil in the pair of radially opposed microcoils.

47 Claims, 6 Drawing Sheets

MICROCOIL DEVICE WITH A FORWARD FIELD-OF-VIEW FOR LARGE GAIN MAGNETIC RESONANCE IMAGING

This application is a continuation in part of Ser No. 09/448,720 filed Nov. 24, 1999, which is a CIP of Ser. No. 09/131,031 filed Aug. 7, 1998, which is a CIP of Ser. No. 08/916,596 filed Aug. 22, 1997 U.S. Pat. No. 5,964,705.

BACKGROUND OF THE INVENTION

1. Field of the Invention

This invention relates to primary medical devices for the reception of radio frequency electromagnetic radiation, particularly medical devices used to obtain a magnetic resonance image of a region in front of the device and within a natural organism or patient (such as within a human) or elsewhere, and secondary medical devices such as catheters and secondary devices for delivery of therapeutic agents and monitoring of metabolic activity. The use of magnetic resonance primary medical devices to provide enhanced imaging within the region of interest in conjunction with the deployment of secondary medical devices offers a particularly effective means of delivering targeted therapy.

2. Background of the Invention

In the practice of the present invention, the term MR microcoil is used to denote a magnetic resonance device used for imaging internally from a patient. This term is in contrast to MR coils that are conventionally used externally to the body for MR imaging purposes. The MR microcoil may be mounted at the tip of a catheter or other insertion device used to probe the interior of a body. The combination of the microcoil mounted on another device provides quick and direct access to the region where imaging is required. Medical procedures such as image-guided and minimal access surgery, performed within small regions of a patient's anatomy, demand the ability to visualize the internal terrain and/or the procedure being performed by the surgeon. When the secondary medical device is also intentionally altering the molecular content in the neighborhood of the anatomical region being treated or infused with therapeutics, it is also important to be able to determine the direction and amount of change in the molecular content. While alternative methods, including x-ray imaging and fiber optic viewing offer possible alternative means of performing the visualization of terrain and the location of physical secondary devices, magnetic resonance imaging methods are a particularly convenient means of doing this, especially given the highly localized nature of the procedures being performed. In addition, as described in U.S. patent applications Ser. Nos. 08/857,043 and 08/856,894 filed on May 15, 1997, the use of improved Magnetic Resonance Imaging (MRI) techniques and devices enables a real-time visualization of compositional changes in the molecular composition of small regions within patients. The compositional changes may be caused by delivery of drugs or active chemicals, or by the stimulation of local chemical production by tissues or organs in the patient. MRI can actually enable visualization of minute concentration changes within the body, particularly intracranial regions of the patient.

Limitations exist with other imaging modalities, such as x-rays or fiber optics. For example, extended x-ray exposures are harmful to the patient, and fiber optic equipment is not well suited either to viewing within small confines or to volume visualization. Both of these limitations in the alternative technologies are circumvented by magnetic resonance imaging.

U.S. Pat. No. 5,271,400 describes a tracking system for the position and orientation of an invasive device within a patient. The device includes a receiver coil and an MR active sample. The receiver picks up magnetic resonance signals generated by the sample. The frequencies are proportional to the location of the coil along the applied field gradients, since the signals are received in the presence of these magnetic field gradients. The system is designed to enable location of the invasive device and enhanced imaging of a region around the invasive device is not a functionality intended for this device.

In 'MR imaging of blood vessels with an intravascular coil', J. Mag. Res. Imag., 1992, Vol.2, pages 421–429, A. J. Martin, D. B. Plewes and R. M. Henkelman describe an opposed solenoid design for an intravascular MR microcoil. This paper describes microcoils made of a pair of helical windings arranged in opposed fashion at the tip of a catheter, shown to be suitable for magnetic resonance imaging purposes. The term "opposed coil" means a coil in which the relative winding of two coil segments is opposite in sense, and the current flow in each opposed coil winds in opposite directions about the coil axis (relative to moving towards or away from the core or axis of the coil). That is, viewing the coils looking down an axis of the core around which the coils are disposed, one will be wrapped clockwise and the other will be wrapped counterclockwise, with a common lead between the two segments. The field-of-view of this coil is roughly cylindrical about the opposed solenoidal windings. The coil is essentially radio frequency insensitive beyond the longitudinal extent of the windings since the magnetic field in this design is squeezed out of the gap between the windings and is only significantly large in a cylindrical region that does not extend too far beyond this gap.

E. Atalar et al. describe a catheter receiver coil in 'High resolution MRI and MRS by using a catheter receiver coil', Mag. Res. Med., 1996, Vol. 36, pages 596–605. This design uses essentially a long wire looped back on itself inside a catheter so that the conductor functions in effect as a transmission line. The sensitivity of this receiver design is affected by the conductor length. In addition, the region of sensitivity surrounds the coil, and does not extend forward beyond the coil.

U.S. Pat. No. 4,572,198 describes a catheter for use with magnetic resonance imaging systems. The catheter includes a wound coil for exciting a weak magnetic field at the catheter tip. This structure provides a local distortion of the MR image, yielding an image cursor on the magnetic resonance imaging display. This design is not intended for high-gain applications.

In U.S. Pat. No. 5,964,704, Truwit and Liu discuss an opposed solenoid design for an MR microcoil with helical windings whose pitch varies along the length of the winding with the aim of achieving homogeneity or control of the field generated by the coils. The field of view is not addressed in this patent document, although the central region of view is enhanced and may be controlled by application of the principles described in that patent.

A copending, commonly assigned U.S. patent application Ser. No. 09/532,145 filed the same date as this application and entitled "A Device for High-Gain and Uniformly Localized magnetic Resonance Imaging" by R. Viswanathan and R. Raghavan describes a horn-shaped coil designed to maximize receptive field homogeneity within the field of view (which is a roughly cylindrical region surrounding the coil), which field of view does not extend forward beyond the coil.

A microcoil device for producing a very high-gain signal in a wide field of view in a cylindrical region surrounding the coil, but not forward to it, was described by R. Viswanathan in a second U.S. patent application Ser. No. 09/532,667.

Although recent technology has clearly advanced the image enhancing capability of secondary medical devices in regions perpendicular to the axis of the core of the windings on the secondary medical device, there is always further need in the art to expand the field and regions where images can be enhanced.

SUMMARY OF THE INVENTION

While microcoils for internal imaging have been described before, the device of the present invention advances the state of the art by design features that maximize the field of view in a direction forward to and beyond the spatial extent of the coil itself (e.g., parallel to the axis or the core of the device), as well as improving the signal gain within this field of view. The signal power falls off with distance in the forward direction (forward being defined as a direction outwardly directed from the device along the core axis of the microcoils). For volume imaging purposes, this fall-off can be adjusted for by dividing the reconstructed image intensity at a given voxel location by the gain corresponding to that voxel (which is proportional to the magnetic field B at that location), and repeating this for all voxels.

An aspect of the invention comprises a device to be inserted into a patient comprising a solid body having at least one microcoil, or at least one pair of radially opposed microcoils physically associated with the solid body, each microcoil having an outside microcoil diameter of 6 mm or less, all individual windings of said each microcoil together defining a geometric plane of each microcoil, and the plane of each microcoil being parallel to the plane of another microcoil in each pair of radially opposed microcoils.

DESCRIPTION OF THE INVENTION

Figure 1:
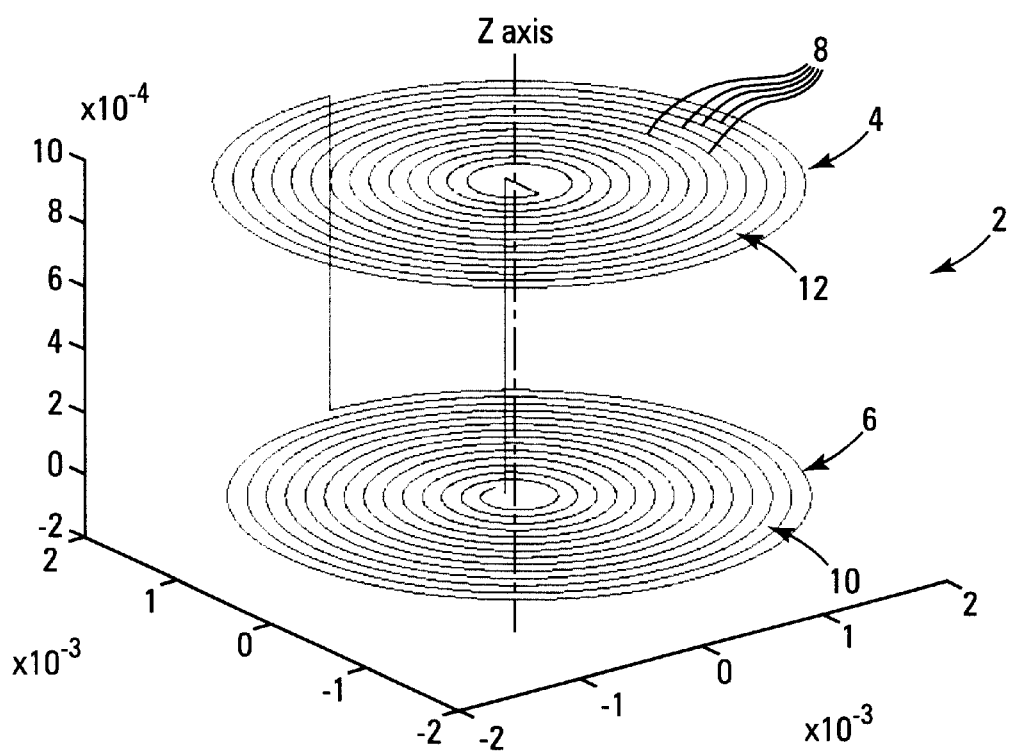
FIG. 1 shows a three dimensional plot of the microcoil geometry with a single pair of radially-opposed spirals.

The detailed description in the following makes reference to the accompanying drawings which form a part hereof, which are included for illustration of the specific embodiments in which the invention may be practiced. These embodiments are described in sufficient detail to enable those skilled in the art to practice the invention, and it is to be understood that other embodiments may be utilized and that structural, configurational, logical, physical, architectural and electrical changes may be made without departing from the spirit and scope of the present invention.

The practice of certain aspects of the present invention are applicable to all medical devices which might be used with magnetic resonance imaging-based viewing procedures occurring concurrently with the primary medical procedure. Features of the present invention which may individually have this general applicability within the medical device field include the types of RF-responsive coils and associated circuitry provided to medical devices to assure their MR-compatibility, and means for directing the said microcoil within or with a catheter device. One form of construction in the practice of the present invention uses a single electrically conducting path, configured so as to yield one microcoil spiral winding or a multiplicity of pairs of spiral windings with a common coil axis, with the spirals in each pair being radially opposed. The term "radially opposed" as used in the practice of the present invention is defined as meaning that the pairs have their windings positioned in the sense that one member of each spiral pair winds radially inward and the other member of the pair winds radially outward about the coil axis (when moving along the length of a continuous electrical path). There cannot be an intermediate coil between the two coils of the pair of radially opposed coils that has an opposite winding sense if those two microcoils are to be considered 'radially opposed' in the practice of the invention, or those adjacent coils would not be radially opposed with a uniform sense of winding. The term "radially-opposed" will be used to describe this arrangement of each spiral pair (that is a pair on a common coil axis) with the spirals in each pair being radially opposed in the sense that one member of each spiral pair winds radially inward and the other member of the pair winds radially outward about the coil axis when considered along a common, continuous electrical path. The electrical path need not be continuous (e.g., the same current passing through one microcoil and then the other in the path) for a radially opposed pair to be formed. For example, there may be two separate conductive paths from the same direction. One electrically conductive path may connect to the exterior winding of a microcoil, and the other electrically conductive path may connect to the interior winding of the adjacent microcoil. These adjacent microcoils could then be considered radially opposed. It is important to note, however, that the sense of the winding of each of the spirals in the entire configuration or at least at one end of a configuration or at one end of a device is the same (all clockwise or all anti-clockwise about the coil axis as seen from the proximal end of the coil, looking down the axis).

Another unique feature of the present invention is the potential for use of multiple radially-opposed spiral pairs in a single electrically conducting path and all wound with the same sense of winding. Thus, even widely separated pairs of spirals in this arrangement would have the same winding sense, although sufficiently separated pairs of coils at distant positions along a single device could have pairs with different winding senses, especially where the distance is great enough that there would not be a significant (greater than 10%) overlap in magnetic fields of MRI significance. This winding configuration allows for a significantly large receptive field in a roughly cylindrical region forward from the distal end of the microcoil or forward from the catheter when the microcoil is placed at the distal tip of the catheter. The gain in these regions falls off with increasing distance from the distal end of the microcoil device. The gain is significantly large in a cylindrical region of length of more than 2 cm beyond the distal end of the coil, and of diameter more than 2 cm around the coil axis. Within a distance of 1 cm forward from the distal end of the coil, the average improvement in signal-to-noise ratio with a single radially-opposed spiral pair can be larger by a factor of about 40 compared with the typical construction of a standard head coil. At a distance of 2 cm forward from the distal end of the coil, the signal-to-noise ratio with the use of a single spiral pair is comparable to that obtained with a standard head coil. The use of radially-opposed spiral pairs allows for optimally squeezing forward the magnetic field produced by a current in the conductor, and thence the increased sensitivity in the forward direction.

An aspect of the invention comprises a device to be inserted into a patient comprising a solid body having at least one pair of radially opposed microcoils physically associated with the solid body, each microcoil having an outside microcoil diameter of 6 mm or less, all individual windings of said each microcoil together defining a geometric plane of each microcoil, and the plane of each microcoil being parallel to the plane of another microcoil in the pair of radially opposed microcoils. Parallelism and planarity of microcoils are approximate and do not have to be mathematically precise. For example, it would be difficult to have every single winding (a single complete encirclement around an axis or core) exactly and uniformly concentric about that core or preceeding windings and within a single plane with every other winding within a microcoil. The fact that the elongated element (e.g., wire) that constitutes the winding is three-dimensional means that a literally two-dimensional plane cannot exist that encompasses all dimensions of the winding. There may also be some wobble or axial shifting of windings. Similarly, parallelism between the planes of adjacent microcoils allows for some significant (e.g., 10–20 degrees) angularity between the planes defined by the windings in the microcoil, and absolute parallelism, although probably desirable, is neither likely nor essential.

In the practice of the present invention, the direction pointing along the catheter (or microcoil) axis from the proximal end of the microcoil to the distal end of the microcoil will be referred to as the 'forward' direction. The forward direction will often be associated with the forward tip of the catheter or medical element also. The large forward extension of the field of view and the high sensitivity of the coil in a significantly larger region within the field of view constitute a substantial advance in the design of magnetic resonance microcoils.

Besides the monitoring of small quantities of locally delivered therapeutic agents, including those used in gene and cell based therapies, an important application area of the microcoil described herein is the monitoring of cell and tissue function by means of magnetic resonance spectroscopy methods, which can directly measure expression levels of biological and labeling molecules and metabolic activity in tissue. A description of applications in these areas may be found in "Principles of nuclear magnetic resonance microscopy", P. T. Callaghan, Oxford Press, New York, 1991.

FIG. 1 shows a three dimensional view of the preferred microcoil geometry where the radially-opposed geometry of the windings 4 and 6 in the spirals is apparent. In the figure, a coordinate system is chosen such that the z-axis is along the axis of the coil (or the catheter axis). The distance between the individual windings 8 in the spirals of a radially-opposed pair 2 may range from about 0.6 mm to 4 mm. The spiral winding of the first coil 10 may be represented by the equation $$x=-r(\theta) \sin \theta$$

$$y=r(\theta) \cos \theta$$

with $$r(\theta)=r0+(k/2\pi)\theta$$

where k is a constant, x and y are the Cartesian coordinates, r0 is the beginning radius and θ is the winding angle. The winding angle for the spiral goes from 0 to 2πn where the winding number n may be as small as 1 or as large as 25; the representation may be similar for the other spiral 12. The beginning radius r0 can lie in the range between 0.07 mm and 1.7 mm and more preferably between 0.09 mm and 1.4 mm. The constant k can range from 0.02 mm and 1.7 mm or more preferably between 0.03 mm and 1.3 mm or still more preferably between 0.05 mm and 1 mm. Similar values apply for the second spiral of the pair except that the radius of the second coil decreases as $$r(\theta)=r0-(k/2\pi)\theta$$

The entire diameter of the coil may range from 0.3 mm to 6 mm, and more preferably may lie between 1 mm and 4.5 mm. The conductor used in the winding may be an electrically highly conducting material that is capable of being shaped or wound into a microcoil or spiral, such as copper, silver or gold, or it may be suitable alloys or plated composites, polymers, or combinations of highly conducting materials. The thickness of the conductor used in the windings generally may range from 0.05 mm to 2 mm, but this size is dependent upon the selection of the material and the particular needs of the device.

The sensitivity or gain of the coil is proportional to the component of the magnetic field that is transverse to the main field of a magnetic resonance imaging system, produced by unit current flowing through the coil. It is assumed for definiteness below that the microcoil's central axis is parallel to the main magnetic field, although it is straightforward to relax this assumption and allow for a more general relative orientation. The magnetic field may be determined in a specified region surrounding the coil by using the Biot-Savart law:

$$B=(\mu/4\pi)\Sigma[(dl\times r)/(r^3)]$$

with the integral [Σ] taken over the entire length of the coil, where B is the magnetic field at a specified point in space, dl is a current-carrying length element and r is the distance vector from the current element to a specified point.

A study of the distribution of the magnetic field around the coil is useful for assessing the quality of the receptive field. In particular, with the choice of coil orientation with respect to the main magnetic field of the imaging system as stated above, it is the component of the magnetic field transverse to the main magnetic field, and therefore in the x–y plane, that is relevant for signal construction. For this purpose, we have therefore computationally mapped the transverse component of the magnetic field along sections transverse to the coil axis and distal to the distal end of the coil.

Figure 2:
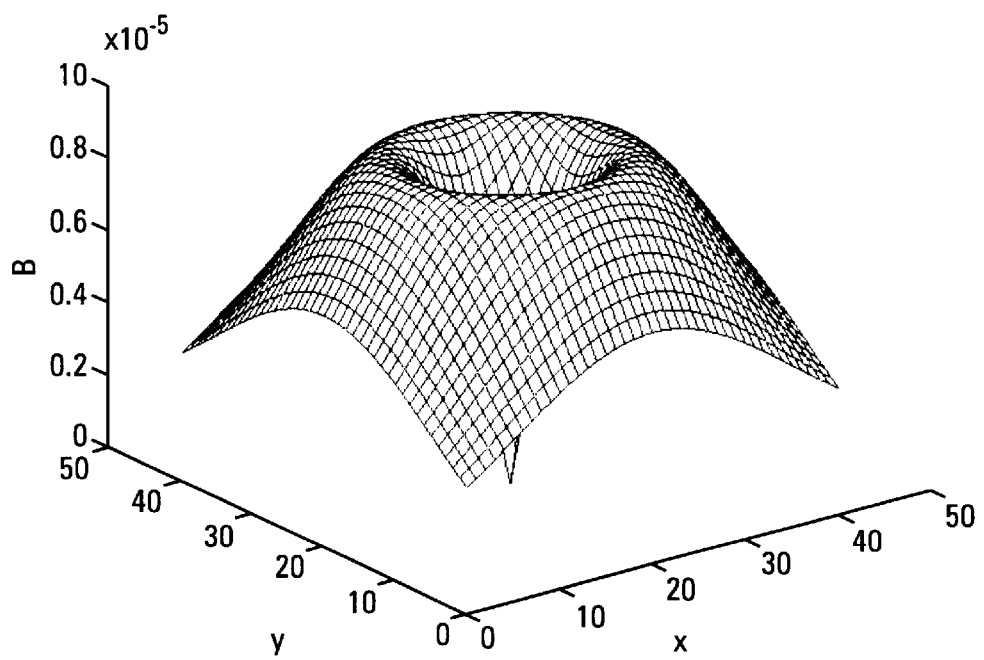
FIG. 2 shows a plot of the transverse magnetic field in a 2 cm×2 cm planar region placed symmetrically about the axis of the coil at a distance of 1 cm forward from the distal end of the coil.

FIG. 2 is a plot of the transverse magnetic field in a 2 cm×2 cm transverse section located at a distance of 1 cm measured from the distal end of the coil. Coil dimensions as in FIG. 1 were used in this computation. The transverse field is minimal at the center of the chosen section and reaches a maximal value in a rotationally symmetric fashion about the center of the section. The significance of the plot is that the transverse field profile, and thence the sensitivity, is still substantial at the outer edges of this section.

Figure 3:
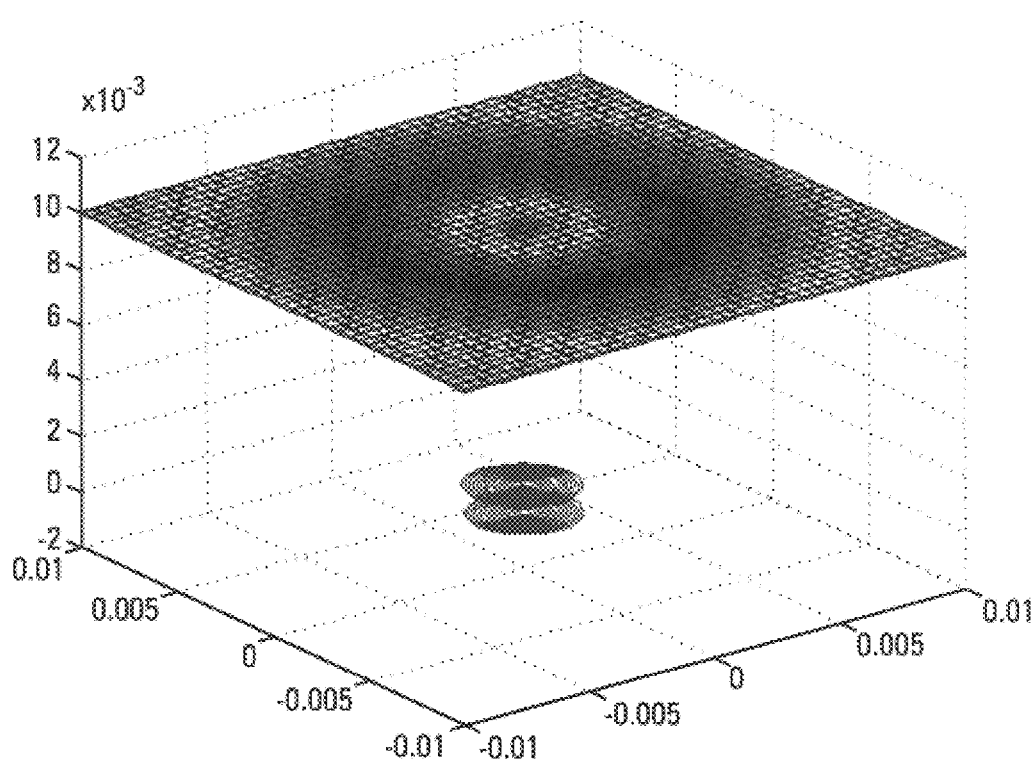
FIG. 3 indicates the location with respect to the coil of the planar region chosen to make the plot in FIG. 2. For clarity, the variation in transverse magnetic field intensity across the chosen planar region is shown here as a variation in color within the slice.

FIG. 3 illustrates the location of the slice chosen in FIG. 2 (over which the magnetic field is plotted there) with respect to the coil. The variation of the magnetic field over the slice is also depicted here by means of a color density, with the spectrum of colors from violet to red indicating a variation in intensity from low to high respectively. For illustration of scale the coil is also shown in this Figure.

Figure 4:
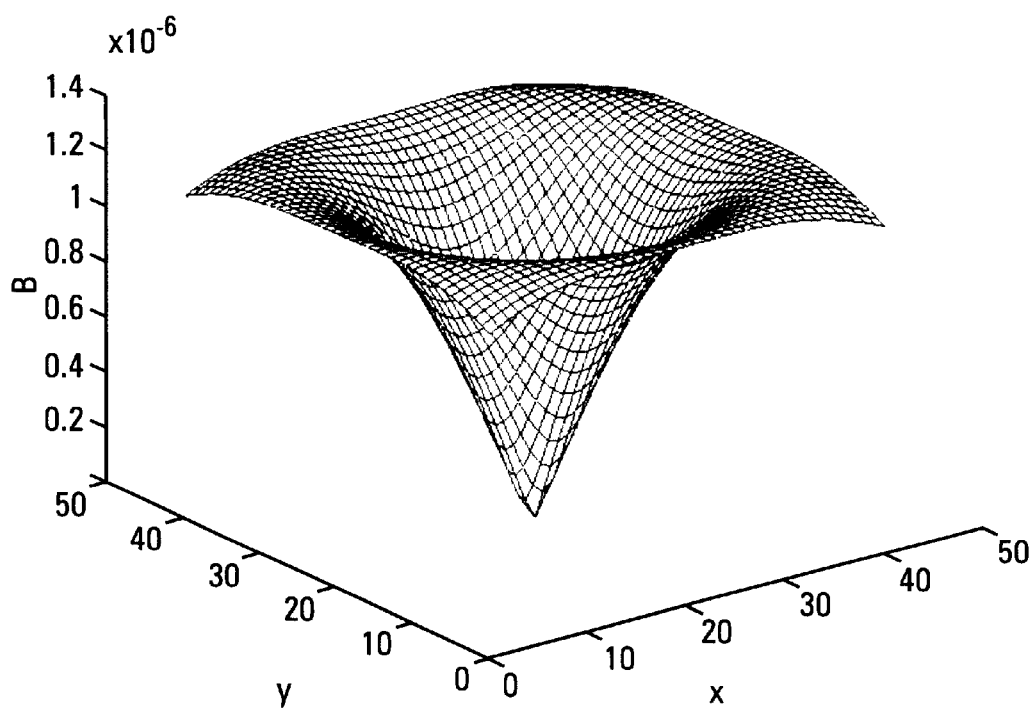
FIG. 4 shows a plot of the transverse magnetic field in a 2 cm×2 cm planar region placed symmetrically about the axis of the coil at a distance of 2 cm forward from the distal end of the coil.

FIG. 4 is similar to FIG. 2 except that it is the transverse field profile at a section located at a distance of 2 cm distal to the distal end of the coil. At this distance the average signal-to-noise ratio attained is comparable to that of a typical commercial head coil.

Figure 5:
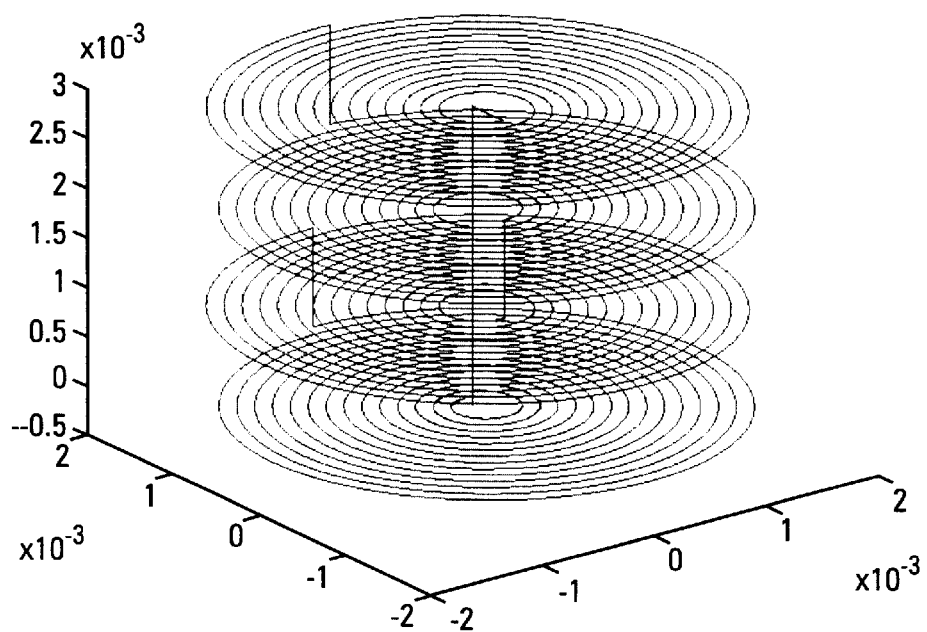
FIG. 5 is a three dimensional plot of the microcoil geometry employing two pairs of radially-opposed spirals.
Figure 6:
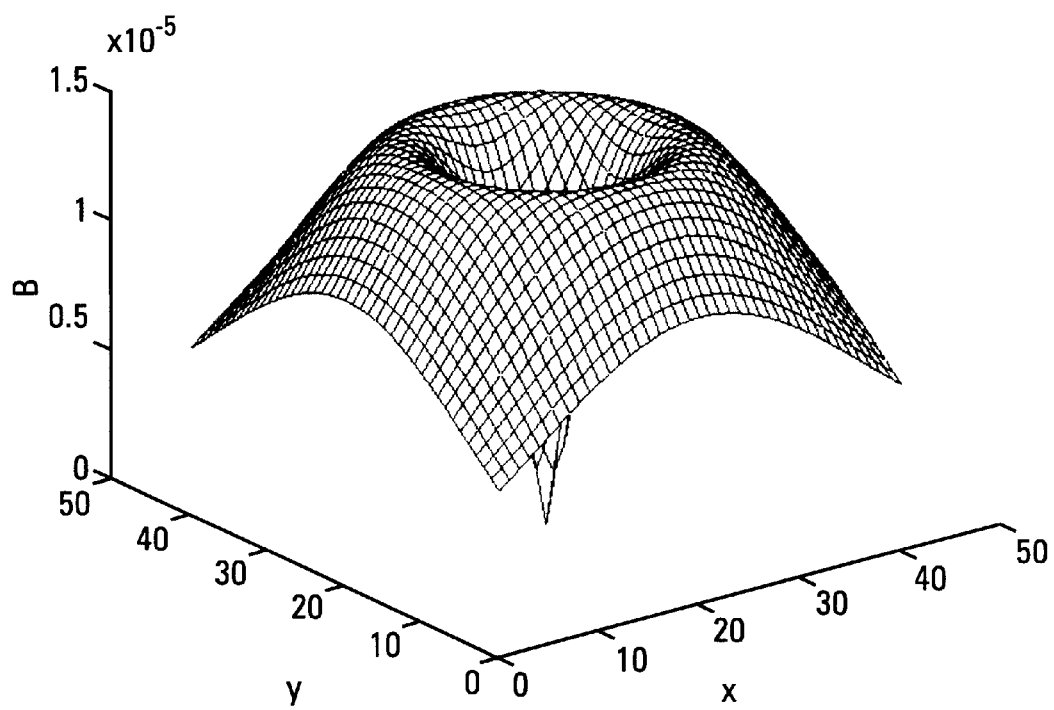
FIG. 6 shows a plot of the transverse magnetic field in a 2 cm×2 cm planar region when two spiral pairs are used, with the planar region placed symmetrically about the axis of the coil at a distance of 1 cm forward from the distal end of the coil.

Multiple pairs of radially-opposed spirals may be employed for further enhancement of signal-to-noise, and to extend the field-of-view in the forward direction. Thus the number of spiral pairs actually used may range from 1 to 20, and more preferably from 1 to 10. As an example, FIG. 5 shows, in a three dimensional perspective, a microcoil configuration 20 which employs two pairs (22 and 24) of radially-opposed spirals (e.g., 26 and 28 for opposed spiral pair 22), which effectively increases the signal-to-noise ratio within the sensitive region or the receptive field corresponding to that provided by the coil by more than 50 percent as compared to a single radially-opposed spiral pair. This effect is further highlighted in FIG. 6, which shows the transverse field in a section located 1 cm forward from the distal end of the coil. The enhancement of the magnetic field is apparent.

The fabrication of the coil may be accomplished using many different methods familiar to those skilled in the art, including winding conducting wires or filaments of wire, deposition and etching processes, masked deposition, microlithography, and such other techniques known to practitioners of the art, on different substrates, including flexible films or a preformed catheter core, and possibly followed by rolling or coiling to achieve the final configuration of the coil geometry. As stated earlier, the conductor may be of any suitable conductive material that may be formed into a coil, such as by way of non-limiting examples, copper, silver, gold or other electrically highly conducting material possibly including alloys, blends, composites or platings. The coil itself may be enclosed by or encased within tightly fitting protective or insulating material such as a polymer. If deposited on a substrate of polymer film, the film may be rolled around a polymer core in order to yield a mechanically rigid geometry. If single strips of film are used as a substrate for each distinct spiral in the design, the ends of conducting strips deposited on the film strips may be microsoldered, connected by through-holes or posts, or otherwise electrically connected together to make up a continuous wound conductor for each pair of opposed microcoils. While the use of radially opposed spiral pairs is a preferred embodiment, the use of spirals in pairs is not essential, and other numbers of sets of spirals ranging from 1 to 15 may also be employed, whether some of these are radially opposed with respect to the rest or not. The geometric planes do not, of course have to have the individual windings in perfect alignment within a plane to function. Some significant amount of deviation from planarity may be quite useful. For example, at least 50 number percent (preferably at least 60%, or at least 75% by number) of windings should lie within 20 degrees or within 15 degrees or within 10 degrees of planarity. The specific geometry of the leads connecting to the microcoil may be fashioned in such a manner as may be convenient for the corresponding application for which the invention is used.

What is claimed is:

1. A device adapted to be inserted into a patient, the device comprising a solid body having at least one pair of radially opposed microcoils physically associated with the solid body, each microcoil having an outside microcoil diameter of 6 mm or less, individual windings of said each microcoil together defining a geometric plane for each microcoil, and the plane of each microcoil being parallel to the plane of another microcoil in the pair of radially opposed microcoils.

2. The device according to claim 1 wherein in the presence of a continuous electrical path, at least one pair of radially opposed microcoils form a spiral pair wherein one microcoil of every spiral pair is wound radially inward and the other microcoil of that pair is wound radially outward about the coil axis, with all microcoils of the spiral pair having the same sense of winding about a common axis of the spiral pair.

3. The device of claim 1 wherein said geometric plane is a plane defined by averaging individual microcoil positions, and at least 80% by volume of all windings within said microcoil lie within 2 mm of the geometric plane.

4. The device of claim 3 wherein said device comprises a catheter having at least one lumen, and said at least one pair of radially opposed microcoils.

5. The device of claim 3 wherein at least one drug delivery port is present within said device.

6. The device of claim 3 wherein said at least one microcoil is embedded within a binder material.

7. The device of claim 3 wherein said at least one pair of microcoils is electrically connected to a preamplifier attached to a portion of said device that may be inserted into an organism.

8. The device of claim 7 wherein said at least one microcoil is embedded within a binder material.

9. The device of claim 1 wherein the sense of the windings and a source of current for said windings are electromagnetically related so that a magnetic field generated by passing current through at least one pair of radially opposed microcoils will extend in a direction that is more distal from a geometric center of said solid body than said pair of radially opposed microcoils.

10. The device of claim 9 wherein said device comprises a catheter having at least one lumen and said at least one pair of radially opposed microcoils.

11. The device of claim 9 wherein at least one drug delivery port is present within said device.

12. The device of claim 9 wherein said at least one pair of microcoils is electrically connected to a preamplifier attached to a portion of said device that may be inserted into an organism.

13. The device of claim 12 wherein said at least one microcoil is embedded within a binder material.

14. The device of claim 1 wherein there are from 2 to 6 pairs of radially opposed microcoils physically associated with said device.

15. The device of claim 14 wherein said device comprises a catheter having at least one lumen, and said at least one pair of radially opposed microcoils.

16. The device of claim 14 wherein at least one drug delivery port is present within said device.

17. The device of claim 14 wherein said at least one pair of microcoils is electrically connected to a preamplifier attached to a portion of said device that may be inserted into an organism.

18. The device of claim 1 wherein said device comprises a catheter having at least one lumen and said at least one pair of radially opposed microcoils.

19. The device of claim 1 wherein at least one drug delivery port is present within said device.

20. The device of claim 1 wherein said at least one microcoil is embedded within a binder material.

21. The device of claim 1 wherein said at least one pair of microcoils is electrically connected to a preamplifier attached to a portion of said device that may be inserted into an organism.

22. The device of claim 1 wherein said geometric plane is a plane defined by mathematically averaging individual winding positions, and at least 80% of all windings within said microcoil lie within 2 mm of the geometric plane.

23. The device of claim 1 wherein the sense of the windings and a source of current for said windings are electromagnetically related so that a magnetic field generated by passing current through said at least one pair of opposed microcoils will extend in a direction that is more distal from a geometric center of said solid body than said pair of opposed microcoils.

24. The device of claim 1 wherein there are from 2 to 6 pairs of opposed microcoils physically associated with said device.

25. A method of generating an electromagnetic RF receptive field exterior to a device comprising:
providing a device comprising a solid body having a geometric center and a distal end, with at least one pair of radially opposed microcoils physically associated with the solid body at said distal end, each microcoil having an outside microcoil diameter of 6 mm or less, the individual windings of said each microcoil defining a geometric plane, and the plane of each microcoil being parallel to the plane of another microcoil in the pair of radially opposed microcoils;
providing a radio frequency field around said device; and
generating an RF responsive spatial region extending from said at least one pair of opposed microcoils toward or beyond said distal end.

26. A device adapted to be inserted into a patient, the device comprising a solid body having at least one pair of opposed microcoils physically associated with the solid body, each microcoil having an outside microcoil diameter of 6 mm or less, collective individual windings of said each microcoil defining a geometric plane, and the plane of each microcoil being parallel to the plane of another microcoil in the pair of opposed microcoils.

27. The device of claim 26 wherein said device comprises a catheter having at least one lumen, and said at least one pair of opposed microcoils.

28. The device of claim 26 wherein at least one drug delivery port is present within said device.

29. The device of claim 26 wherein said at least one microcoil is embedded within a binder material.

30. The device of claim 26 wherein said at least one pair of microcoils is electrically connected to a preamplifier attached to a portion of said device that may be inserted into an organism.

31. A device adapted to be inserted into a patient, the device comprising a solid body having at least one pair of opposed microcoils physically associated with the solid body, each microcoil having an outside microcoil diameter of 6 mm or less, at least 50 number % of individual windings of said each microcoil lying within a geometric plane, and the geometric plane of each microcoil being parallel to the plane of another microcoil in the pair of opposed microcoils, and there being at least four windings within each microcoil in said at least one pair of opposed microcoils.

32. A method of generating an electromagnetic RF responsive field exterior to an device comprising:
providing a device comprising a solid body having a geometric center and a distal end, with at least one pair of opposed microcoils physically associated with the solid body at said distal end, each microcoil having an outside microcoil diameter of 6 mm or less, the geometrically averaged position of individual windings of said each microcoil defining a geometric plane, and the plane of each microcoil being parallel to the plane of another microcoil in the pair of opposed microcoils;
providing a changing magnetic field around said at least one pair of opposed microcoils to generate an electrical signal in said microcoils; and
a responsive field from said microcoils extending from said at least one pair of opposed microcoils towards or beyond said distal end.

33. A method of generating an electromagnetic RF responsive field exterior to an device comprising:
providing a device comprising a solid body having a geometric center and a distal end, with at least one pair of opposed microcoils physically associated with the solid body at said distal end, each microcoil having an outside microcoil diameter of 6 mm or less, at least 50 number % of individual windings of said each microcoil lying within a geometric plane;
causing a change in a magnetic field around said device to generate a field response from said microcoils; and
a responsive field extending from said at least one pair of opposed microcoils towards or beyond said distal end.

34. A device adapted to be inserted into a patient the device comprising a solid body having at least one pair of radially opposed microcoils physically associated with the solid body, each microcoil having an outside microcoil diameter of 6 mm or less, with at least one pair of opposed microcoils physically associated with the solid body at a distal end, at least 50 number % of individual windings of said each microcoil lying within a geometric plane.

35. A device adapted to be inserted into a patient, the device comprising a solid body having at least one pair of radially opposed microcoils physically associated with the solid body, each microcoil having an outside microcoil diameter of 6 mm or less, all individual windings of said each microcoil lying within a geometric plane, and the plane of each microcoil being parallel to the plane of another microcoil in the pair of radially opposed microcoils.

36. A device adapted to be inserted into a patient, the device comprising a solid body having at least one microcoil physically associated with the solid body, each microcoil having an outside microcoil diameter of 6 mm or less, the individual windings of said each microcoil lying within a geometric plane.

37. The device of claim 36 wherein said geometric plane is a plane defined by averaging individual microcoil positions, and at least 80% of all windings within said microcoil planes are parallel to said geometric plane within 2 mm of the geometric plane.

38. The device of claim 36 wherein the sense of the windings and a source of current for said windings are electromagnetically related so that a magnetic field generated by passing current said at least one microcoil will extend in a direction that is more distal from a geometric center of said solid body than said microcoil.

39. The device of claim 36 wherein there are from 1 to 13 microcoils physically associated with said device.

40. The device of claim 36 wherein said device comprises a catheter having at least one lumen, and said at least one microcoil.

41. The device of claim 36 wherein at least one drug delivery port is present within said device.

42. The device of claim 36 wherein said at least one microcoil is embedded within a binder material.

43. The device of claim 36 wherein said at least one microcoil is electrically connected to a preamplifier within a portion of said device which may be inserted into an organism.

44. A device adapted to be inserted into a patient, the device comprising a solid body having at least one microcoil physically associated with the solid body, each microcoil having an outside microcoil diameter of 6 mm or less, at least 50 number % of individual windings of said each microcoil lying within a geometric plane perpendicular to an axis of said microcoil.

45. A method of generating an electromagnetic RF receptive field exterior to a device comprising:

providing a device comprising a solid body having a geometric center and a distal end, with at least one microcoil physically associated with the solid body at said distal end, each microcoil having an outside microcoil diameter of 6 mm or less, the individual windings of said each microcoil defining a geometric plane;

providing a radio frequency field around said device; and a receptive field extending from said at least one microcoil beyond said distal end.

46. A method of generating an electromagnetic RF receptive field exterior to a device comprising:

providing a device comprising a solid body having a geometric center and a distal end, with at least one microcoil physically associated with the solid body at said distal end, each microcoil having an outside microcoil diameter of 6 mm or less, at least 50% of individual windings of said each microcoil lying within a geometric plane;

providing a radio frequency field around said device; and a receptive field extending from said at least one microcoil beyond said distal end.

47. A device adapted to be inserted into a patient, the device comprising a solid body having at least one microcoil physically associated with the solid body, each microcoil having an outside microcoil diameter of 6 mm or less and a common axis, with at least one microcoil physically associated with the solid body at a distal end, at least 50% of individual windings of said each microcoil lying within a geometric plane perpendicular to said common axis.

* * * * *